United States Patent [19]

Carter, Jr.

[11] 4,413,653
[45] Nov. 8, 1983

[54] INFLATION ANCHOR

[75] Inventor: Ernest E. Carter, Jr., Duncan, Okla.

[73] Assignee: Halliburton Company, Duncan, Okla.

[21] Appl. No.: 309,621

[22] Filed: Oct. 8, 1981

[51] Int. Cl.³ .............................................. F16L 55/12
[52] U.S. Cl. ....................................... 138/89; 73/49.1; 138/93; 277/34
[58] Field of Search .............................. 138/93, 90, 97; 166/179, 187, 192; 220/225, 232, 239, 85 B; 277/34, 34.3; 285/147; 24/136 R, 115 R, 265 EE; 403/265, 267, 5; 73/49.1

[56] References Cited

U.S. PATENT DOCUMENTS

| | | | |
|---|---|---|---|
| 334,711 | 1/1886 | Lorenz | 24/136 K |
| 2,221,775 | 11/1940 | Boynton | 166/187 X |
| 2,516,581 | 7/1950 | Lynes et al. | 166/187 X |
| 2,815,817 | 12/1957 | Conrad | 277/34.3 |
| 3,041,204 | 6/1962 | Green | 138/97 X |
| 3,103,235 | 9/1963 | Stringham | 138/97 |
| 3,477,506 | 11/1969 | Malone . | |
| 3,495,626 | 2/1970 | Nagel | 138/97 |
| 3,529,667 | 9/1970 | Malone . | |
| 3,593,749 | 7/1971 | Reardon | 138/93 |
| 3,604,732 | 9/1971 | Malone . | |
| 3,834,421 | 9/1974 | Daley | 138/93 X |
| 3,844,313 | 10/1974 | Arnold | 403/5 X |
| 3,971,437 | 7/1976 | Clay et al. | 277/34 X |
| 4,077,435 | 3/1978 | Van Scoy | 138/93 |
| 4,079,755 | 3/1978 | Van der Lans | 138/93 |
| 4,280,533 | 7/1981 | Jacobellis | 220/85 B X |
| 4,349,204 | 9/1982 | Malone . | |

FOREIGN PATENT DOCUMENTS 1675362 12/1970 Fed. Rep. of Germany ........ 277/34

Primary Examiner—John W. Shepperd
Assistant Examiner—Mark Thronson
Attorney, Agent, or Firm—Joseph A. Walkowski; Thomas R. Weaver

[57] ABSTRACT

An hydraulically inflatable anchoring device for use in pipelines. A woven fabric of braided steel cable is employed as the outer cover of the device, being expanded and maintained against the inside of a pipeline by inflation of an elastomeric bladder within. The anchoring device is configured in the shape of a dumbbell, with a center section of lesser diameter than the ends, in order to facilitate movement through curved sections of pipe. The woven fabric is wrapped around the ends of the anchoring device and clamped in the interior thereof, so as to provide a greater length of fabric for frictional engagement with the wall of the pipe.

14 Claims, 4 Drawing Figures

INFLATION ANCHOR

BACKGROUND OF THE INVENTION

There are many occasions during the inspection and repair of pipelines when it is necessary to seal off the bore of the pipeline at a given location. For example, a pipeline may require sealing at a certain point in order to patch a leak or allow replacement of a section. In other instances, the pipeline bore may be sealed and the pressure raised behind the sealing device in order to ascertain if a leak exists in a particular pipeline section, the pressure of such leak being indicated by a failure of the pipeline to hold pressure. Several prior art approaches have been taken in the design of such sealing devices.

U.S. Pat. No. 3,593,749 discloses a pipeline pig stopper which relies on mechanical grippers or slips to fix the pig in the pipeline bore, after which an inflatable element is expanded to effect the actual seal. Major disadvantages of such a device include the limitation of gripping power due to the relatively small size and rigid configuration of the grippers, and damage incurred by the interior of the pipe in which the grippers are set. These grippers may not conform exactly to the pipeline bore wall, which may be lined with relatively soft plastics. Such plastics can be easily damaged by the gripper serrations, particularly if the grippers are not perfectly aligned with the bore wall.

U.S. Pat. No. 4,077,435 discloses a pipeline plugging apparatus which relies on stopping mechanisms inserted in the wall of the pipeline to arrest plug movement, subsequently sealing the pipeline bore with an expandable elastomer seal. While effective, the use of such stopping mechanisms necessarily limits the use of such plugs to instances where the pipeline is easily accessible and where a leak has already been located.

U.S. Pat. No. 4,079,755 discloses a rubber-covered inflatable pipeline plug reinforced with tire cord to withstand high inflation pressures. The utilization of an elastomer necessarily limits the anchoring force obtainable by the device, as the elastomer will tend to "creep" at high pipeline pressures, acting like a highly viscous fluid. Such "creep" is extremely undesirable, particularly when an exact pipeline location is desired for repair or leak location purposes.

In addition to the disadvantages noted above, the prior art devices also are extremely limited in their ability to traverse curves in a pipeline, unless they are made extremely short relative to their diameter, and a number of anchors or plugs employed in tandem. This is due in part to the limited expandability of the prior art devices, necessitating outer diameters which place the unset gripping or anchoring means close to the pipeline wall, and in part due to the fact that these devices are of a relatively constant diameter throughout their length.

SUMMARY OF THE INVENTION

The inflation anchor of the present invention comprises an inflatable elastomer bladder mounted on a mandrel, and covered with a woven fabric of braided steel cable. Between the metal fabric and bladder is a layer of tire cord which serves to prevent extrusion of the bladder elastomer through the metal fabric. The inflation anchor is configured in a dumbbell shape when uninflated, with the midsection of lesser diameter than the ends in order to facilitate passage of the device through curves in the pipeline. The metal fabric covers the entire exterior of the anchor body, being wrapped around the ends thereof, tucked and clamped in the interior. These features provide frictional engagement of the metal fabric with the pipeline bore wall along 95% of the anchor body length when the anchor is inflated to a cylindrical shape, resulting in a shorter anchor for a given desired axial holding capacity. The woven metal fabric provides multitudinous frictional engagement points with the bore wall, thus distributing the radial and axial forces over much larger areas, and reducing the incidence and extent of damage to a liner. Furthermore, the use of a metal fabric which is positively secured to the rigid interior of the anchor avoids elastomer tensile yield strength limitations, and the "creep" experienced in prior art devices.

BRIEF DESCRIPTION OF THE DRAWINGS

The inflation anchor of the present invention will be more readily understood by reference to the following detailed description in conjunction with the accompanying drawings, wherein.

DESCRIPTION OF THE PREFERRED EMBODIMENT

Figure 1:
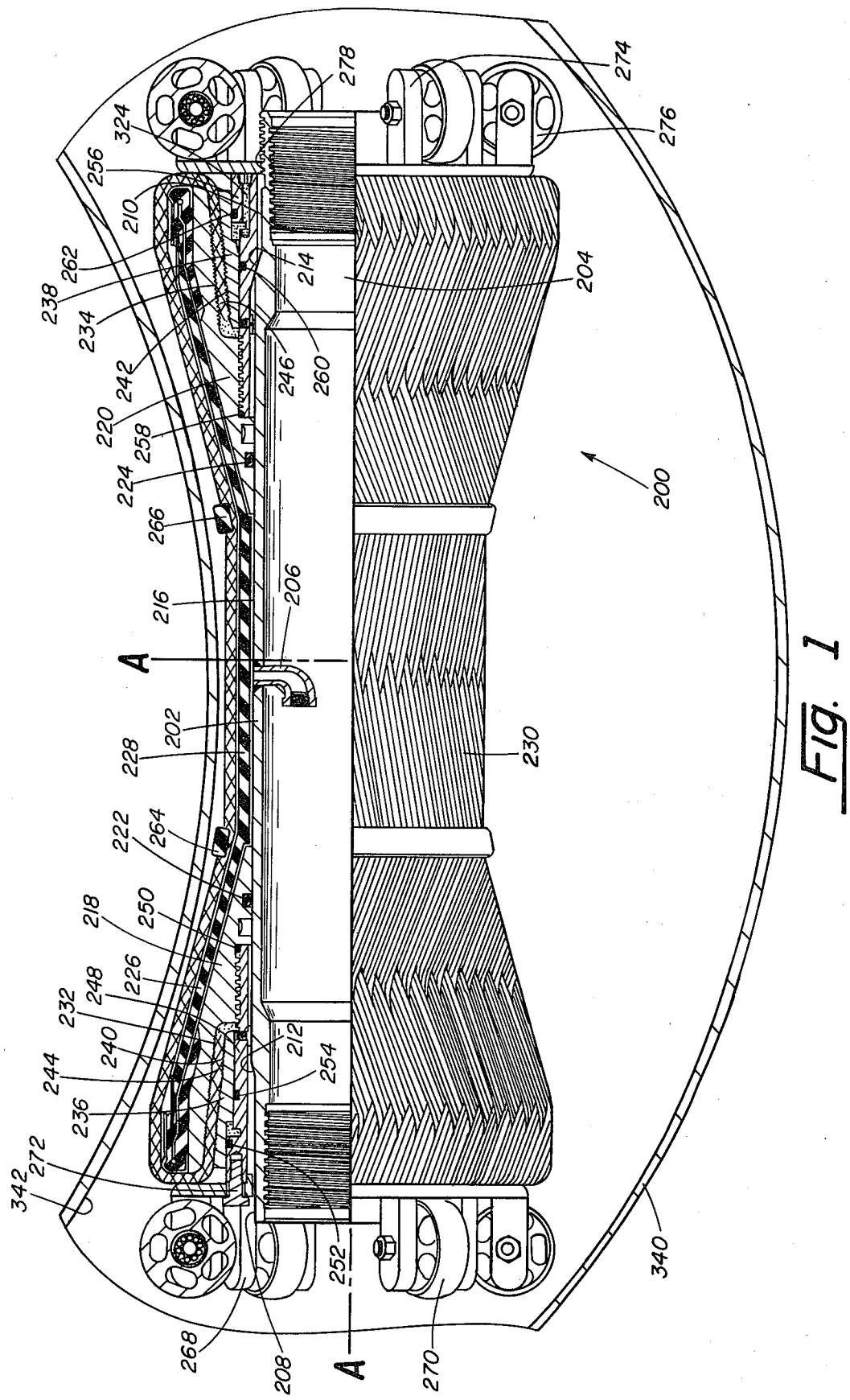
FIG. 1 is a half-section elevation of the inflation anchor of the present invention as moves, uninflated, through a schematically depicted curved section of pipeline.
Figure 4:
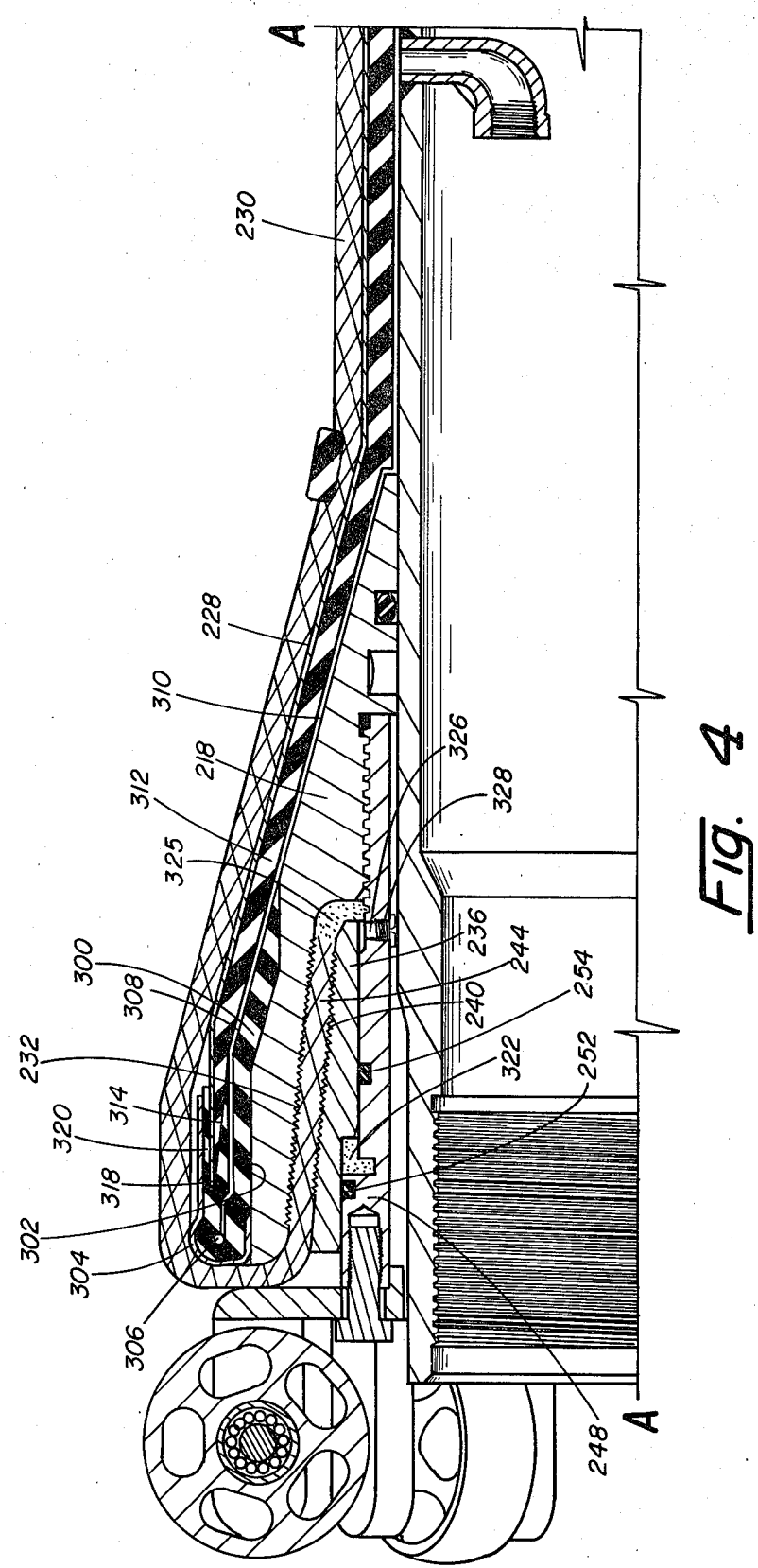
FIG. 4 is an enlarged section of a portion of the inflation anchor of the present invention, taken along lines A—A of FIG. 1.

Referring to FIGS. 1 and 4, the preferred embodiment of the inflation anchor of the present invention is described hereafter.

Inflation anchor 200 comprises mandrel 202 having bore 204 therethrough. Inflation pipe 206 extends through the wall of mandrel 202. The exterior of mandrel 202 possesses arms 208 and 210 of substantially equal diameter at each end, followed by tapered annular surfaces 212 and 214, respectively, that lead to major surface 216 of a constant diameter.

Identical anchors 218 and 220 ride on major surface 216 of mandrel 202, a fluid seal between mandrel 202 and anchors 218 and 220 being effected by O-rings 222 and 224, respectively. Elastomeric bladder 226 envelopes mandrel 202 and extends substantially to the ends of anchors 218 and 220. Two layers of steel tire cord 228 are laid up on the outside of bladder 226, also extending substantially to the ends of anchors 218 and 220. The details of arrangement of bladder 226 and tire cord 228 will be discussed in greater detail hereafter with respect to FIG. 4. Woven steel cable fabric 230 surrounds tire cord 228, and extends beyond end shoes 218 and 220, being wrapped around the ends thereof and tucked against interior serrated surfaces 232 and 234. Wedges 236 and 238, having exterior serrated surfaces 240 and 242, are inserted within anchors 218 and 220, the free ends 244 and 246 of woven steel cable fabric 230 being thereby clamped between each anchor and its cooperating wedge.

At one end of anchor 200, floating end shoe 248 is threaded to anchor 218 to maintain wedges 236 in position as will be more fully explained hereafter. A fluid seal is made between anchor 218 and floating end shoe 248 by O-ring 250, and between wedge 236 and floating end shoe 248 by O-rings 252 and 254. Similarly, at the other end of anchor 200, fixed end shoe 256 maintains wedge 238 in position with respect to anchor 220, as will be more fully explained hereafter. A fluid seal is made between fixed end shoe 256 and anchor 220 by O-ring 258, and between fixed end shoe 256 and wedge 238 by O-rings 260 and 262.

Retractor bands 264 and 266, of elastomeric material, retain anchor 200 in a collapsed mode when not inflated.

Wheel assembly 268 having ball-bearing wheels 270 thereon is secured to floating end shoe 248 by bolts 272. In a similar manner, wheel assembly 274 having ball-bearing wheels 276 thereon is secured to fixed end shoe 256 by bolts (not shown), and is threaded to mandrel 202 as indicated by reference numeral 278.

It may be noted at this time that the woven steel cable fabric 230 may comprise 1/16" 1×19 preformed stainless steel aircraft cable, woven 3 cables per bundle on a 15° bias (included angle) as shown in FIG. 1.

Referring now to FIG. 4, taken on lines A—A of FIG. 1, the arrangement of bladder 226 and tire cord 228 with respect to fabric 230 and the manner of constructing the anchor assembly will be discussed in detail, the description being applicable to both ends of anchor 200. All elastomeric bladder components are preferably formed of natural rubber. Bladder ends 300 of bladder 226 are bonded at 302 to the outer surface of anchor 218. Steel tire cord 304 is tucked under the end of bladder end 300 and folded over, two layers of tire cord being preferable. An O-ring 306 is tucked in the bight of the fold, as shown. Anti-bond paint is applied to outer surface 308 of bladder end 300, inclined surface 310 on anchor 318 and to the surface of the wrap mandrel upon which the anchor assembly is constructed (not shown). Bladder body 312 of bladder 226 is then fitted, there being preferably a one inch overlap 314 between bladder body 312 and bladder end 300. Two layers of steel tire cord 228 are laid up on bladder body 312 at a 15° included angle bias, extending to the end of bladder body at 318. A rubber spacer (location noted generally at 320) is placed over the end of cord 228, tire cord layer 304 then being folded over further into contact with rubber spacer 320. Woven cable fabric 230 is then fitted over tire cord 228, the free end 244 being bent inwardly and tucked under the end of anchor 218. Wedge 236 is then installed, and end shoe 248 threaded to anchor 218. Epoxy resin is then injected into annulus 322 through a longitudinal passage (not shown) extending to the outer end of end shoe 248. Such a passage is shown in end shoe 256 at 324 (see FIG. 1). The epoxy resin is injected preferably at a pressure of at least 1000 PSI through a grease fitting, which causes annulus 322 to enlarge axially and wedge 236 to move inwardly, clamping free end 244 of woven cable fabric 230 securely between serrated surfaces 232 and 240. The resin is maintained in annulus 322 by O-rings 252 and 254. Annulus 325 is then completely filled with epoxy resin through a plurality of apertures 326 spaced radially about the interior of end shoe 248. After filling, pipe plugs 328 are installed. The elastomer (natural rubber) portion of the assembly is then heat cured, which process bonds bladder body 312, bladder end 300, tire cord 228, rubber spacer 320, and tire cord 304 together. The anti-bond paint applied to surface 308 of bladder end 300 and anchor surface 310 prevents bonding at those areas, as well as to the wrap mandrel. The assembly is then placed on mandrel 202, with wheel assemblies secured to each end shoe and in the case of wheel assembly 274, to mandrel 202.

OPERATION OF THE PREFERRED EMBODIMENT

Figure 2:
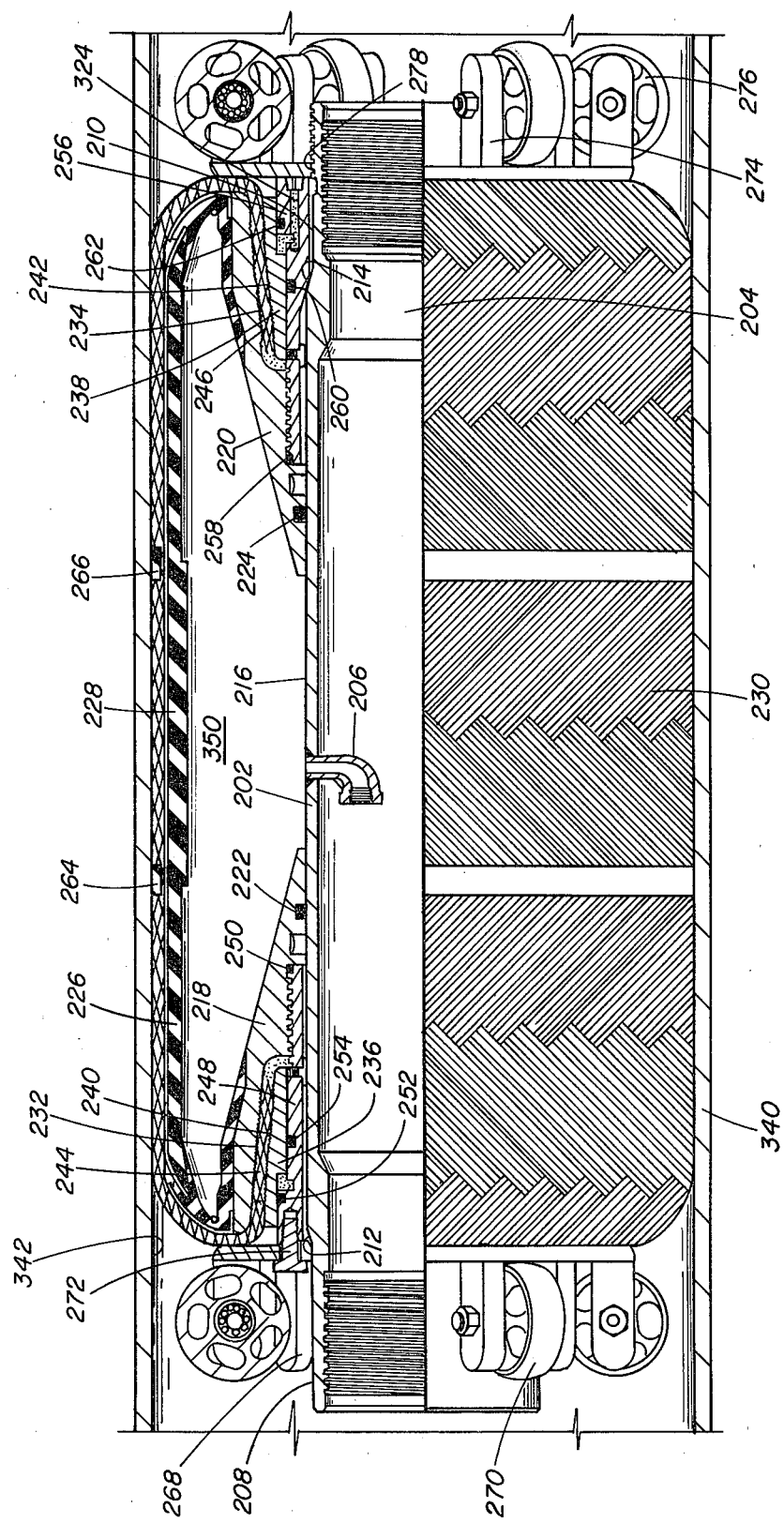
FIG. 2 is a half-section elevation of the inflation anchor of the present invention inflated in a schematically depicted straight pipeline section.
Figure 3:
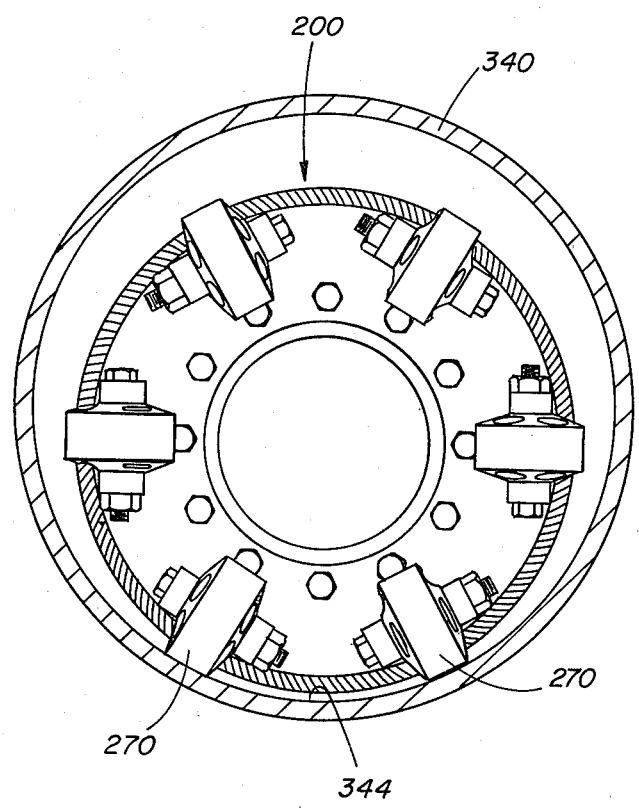
FIG. 3 is an end view of the inflation anchor of the present invention in a straight section of pipeline prior to inflation.

Referring now to FIGS. 1, 2 and 3, the operation of the preferred embodiment of the inflation anchor of the present invention is described in detail hereafter.

Inflation anchor 200 is placed in a pipeline 340 and pumped to the desired location through the action of the fluid in the pipeline on a cup-type device to which inflation anchor 200 is secured, such as procedure being well known in the art. As can be readily seen in FIG. 1, the dumbbell shape of anchor 200 permits it to traverse a horizontal curve of substantially lesser radius than if the device were cylindrical with a substantially constant diameter the same as its outermost extending diameter. Wheels 270 and 276 are not in contact with the side pipeline wall 342 as it traverses the sharp curve, anchor 200 instead sliding along the wall 342 until the radius of curvature decreases enough for wheels 270 and 276 on the side of the anchor to make contact. As can be seen in FIG. 3, inflation anchor 200 rides on its wheels, referenced at 270, as they contact the bottom of pipeline wall 344 throughout its journey in the pipeline (unless an extremely sharp vertical rise or drop is encountered, in which case it will slide as noted above with respect to horizontal curves).

At the desired location, such as is shown in FIG. 2, inflation anchor 200 is inflated at 2500 PSI, for example, through a hydraulic line (not shown) connected to inflation pipe 206. The influx of hydraulic fluid, such as oil, expands elastomeric bladder 226 by creating expanded chamber 350 between mandrel 202, anchors 218 and 220, and the bonded together elastomeric bladder 226. Woven steel fabric 230 contains elastomeric bladder 226, preventing overstressing and rupture thereof. Free ends 244 and 246 are securely clamped between anchors 218 and 220 and their respective wedges 236 and 238. Steel tire cord 228 prevents elastomeric bladder 226 from extruding and rupturing through openings in the weave of fabric 230, which enlarge as inflation anchor 200 expands.

As inflation anchor 200 expands, fixed end shoe 256 remains stationary, being clamped between tapered annular surface 214 and wheel assembly 274, which is threaded to mandrel 202 at 278. Floating end shoe 248, on the other hand, slides axially inwardly upon major surface 216 of mandrel 202 to provide slack for outward radial expansion of fabric 230. As inflation anchor 200 expands and contacts the wall of pipeline 240 throughout its radial extent, wheels 270 and 276 are freed from contact with the pipeline.

When inflation anchor 200 is fully inflated, a substantial axial force can be exerted upon it and any components to which it is connected, without any movement whatsoever. This is due to the extremely large surface area presented by expanded metal fabric 230 for frictional engagement with the pipeline wall. This same large surface area, by preventing multitudinous points for engagement, effectively distributes any axial force applied so that the longitudinal force against any particular portion of the pipeline wall is greatly reduced. The force distribution effect is enhanced by the fabric overwrap and internal clamping, which represents a much longer anchoring element for a given anchor length than is known in the prior art. It is thus apparent that the axial force exerted can be distributed sufficiently to prevent damage to even plastic liners for pipelines, while the anchoring force available is greatly increased. Furthermore, the anchoring force is not limited by the tensile yield strength of the elastomeric bladder, such as is known in the prior art, forcing the present invention from the danger of sudden failure through bladder rupture and the phenomenon of "creep" along the pipeline.

After inflation of the anchor 200, the pipeline may be sealed through use of a cup-type seal, such as would be used to move the anchor through the pipeline, or by an inflatable or expandable elastomer seal such as is known in the art. The desired testing or repair operation may then be performed. Upon completion of the desired operation, inflation anchor 200 is deflated by a release of pressure through inflation pipe 206, retractor bands 264 and 266 collapsing chamber 350 and moving fabric 230 away from contact with the pipeline wall. Anchor 200 and related devices may then be withdrawn from the pipeline.

In lieu of the woven metallic fabric disclosed in the description of the preferred embodiment, it should be understood that a fabric comprising a plurality of overlapping layers of calendered steel cable (cables laid in parallel) may be employed as the frictional element. Such cables may comprise 7×19 preformed stainless steel aircraft cable, the layers of cable being laid on a bias to each other, and at an angle to the axis of the inflation anchor.

It is thus apparent that a novel and unobvious inflation anchor has been disclosed. Furthermore, modifications, deletions and additions to the invention are apparent to one of ordinary skill in the art without departing from the spirit and scope of the claimed invention.

We claim:

1. An inflation anchor adapted for use in a conduit, comprising:
   a substantially cylindrical mandrel;
   an anchor assembly comprising an anchor and a wedge mounted at each end of said mandrel;
   an inflatable elastomeric bladder surrounding said mandrel and each of said anchor assemblies; and
   an expandable fabric of substantially tubular configuration surrounding said bladder, said anchor assemblies and said mandrel, each end of said fabric being wrapped around the longitudinally outermost extremity of each anchor, and tucked against an interior surface thereof, being clamped against said anchor by said wedge.

2. The apparatus of claim 1, wherein one of said anchor assemblies is fixed to said mandrel, the other being slidable thereon.

3. The apparatus of claim 1, wherein said wedges have serrated exterior surfaces thereon, and said anchors have serrated interior surfaces thereon, both adapted to grip said fabric.

4. The apparatus of claim 3, wherein said wedges are driven to clamp said fabric against said anchors by the application of an epoxy resin under pressure.

5. The apparatus of claim 1, wherein said expandable fabric comprises braided metal cable woven into a fabric.

6. The apparatus of claim 5, wherein said braided metal cable comprises 1×19 stainless steel aircraft cable, woven in bundles, three cables per bundle, on a 15° bias.

7. The apparatus of claim 5 further including means for preventing rupture of said bladder disposed between said bladder and said woven fabric, said rupture prevention means adapted to prevent extrusion of said bladder through openings in the weave of said fabric, which openings enlarge as said bladder inflates, forcing said fabric radially outward.

8. The apparatus of claim 7, wherein said means for rupture prevention comprises tire cord.

9. The apparatus of claim 1, wherein the cross-sectional shape of the inflation anchor is that of a dumbbell, with end portions of greater diameter than the mid portion thereof.

10. The apparatus of claim 1 further comprising a plurality of radially spaced wheels at each end of said inflation anchor, said wheels being adapted to facilitate passage of said inflation anchor through said conduit.

11. The apparatus of claim 1 further comprising at least one retractor band circumferentially surrounding said fabric, said at least one retractor band adapted to maintain the center portion of said fabric against said mandrel when said inflation anchor is in an uninflated mode.

12. The apparatus of claim 1 wherein said expandable fabric comprises a plurality of overlapping layers of calendered metal cable.

13. The apparatus of claim 12 wherein said layers are laid on a bias to each other.

14. The apparatus of claim 13 wherein said layers are laid at an angle to the axis of said mandrel.

* * * * *